United States Patent [19]
Wilson et al.

[11] Patent Number: 4,489,203
[45] Date of Patent: Dec. 18, 1984

[54] POLYUMERIC ALKYLENE PHOSPHORIC ACID PIPERAZINE DERIVATIVES AS SCALE INHIBITORS

[75] Inventors: David A. Wilson, Richwood; Druce K. Crump, Lake Jackson, both of Tex.

[73] Assignee: The Dow Chemical Company, Midland, Mich.

[21] Appl. No.: 425,025

[22] Filed: Sep. 27, 1982

[51] Int. Cl.$^3$ .................. C07D 241/04; C02F 5/14
[52] U.S. Cl. .................. 544/337; 210/700; 252/175
[58] Field of Search ........................ 544/337

[56] References Cited
U.S. PATENT DOCUMENTS

| | | | |
|---|---|---|---|
| 2,599,807 | 6/1952 | Bersworth | 260/502.5 R |
| 2,609,390 | 9/1952 | Bersworth | 260/502.5 R |
| 3,331,773 | 7/1967 | Gunderson et al. | 210/698 |
| 3,336,221 | 8/1967 | Ralston | 210/700 |
| 3,434,969 | 3/1969 | Ralston | 210/700 |
| 3,674,804 | 7/1972 | Redmore | 544/337 |
| 3,720,498 | 3/1973 | Redmore | 422/7 |
| 3,743,603 | 7/1973 | Redmore | 252/180 |
| 3,859,211 | 1/1975 | Redmore | 210/729 |
| 3,954,761 | 5/1976 | Redmore | 544/337 |
| 4,051,110 | 9/1977 | Quinlan | 528/244 |

OTHER PUBLICATIONS

Proc. Int. Water Conf., Eng. Soc. West PA., 41, pp. 167–174 (1980) "Toward a Better Understanding of Commercial Organophosphonates", Roderick A. Campbell.

Proc. Int. Water Conf., Eng. Soc., West PA., 39, pp. 89–99 (1978) "Scale and Deposit Control in Cooling Water Systems", Jeffrey R. Townsend, Karl W. Heiman.

Hoechst Organic Chemicals brochure title page and pages 4, 14 and 15.

Primary Examiner—Donald G. Daus
Assistant Examiner—William A. Teoli, Jr.
Attorney, Agent, or Firm—A. C. Ancona

[57] ABSTRACT

New polymers which are the reaction product of aminoethylpiperazine and a dihalo or epoxyhalo compound are subsequently phosphonomethylated to provide products which are useful as threshold ion control agents.

3 Claims, No Drawings

POLYUMERIC ALKYLENE PHOSPHORIC ACID PIPERAZINE DERIVATIVES AS SCALE INHIBITORS

BACKGROUND OF THE INVENTION

The use of methylenephosphonic acid substituted alkylene polyamines for metal ion control at less than stoichiometric amounts was suggested in a patent to Bersworth (U.S. Pat. No. 2,609,390) in 1952. Later a water dispersible polymeric amine chelating agent which included alkylene phosphonate derivatives was indicated as having "threshold" effects in scale inhibition applications (see U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Some other patents which disclose heterocyclic nitrogen containing compounds which are useful as chelating agents and may be employed in threshold amounts are U.S. Pat. Nos. 3,674,804; 3,720,498; 3,743,603; 3,859,211; and 3,954,761. Some of the compounds included therein are heterocyclic compounds having the formulas:

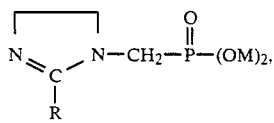

wherein R is hydrogen or alkyl and M is hydrogen, alkali metal, ammonium or a di- or triethanolamine radical;

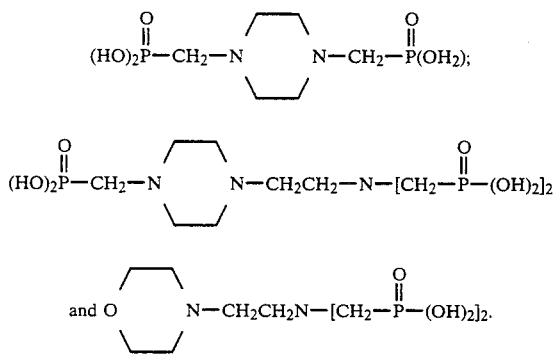

Methylenephosphonates of polyalkylene polyamines, disclosed in U.S. Pat. No. 4,051,110, are made by reacting di- or polyamines with a chain extending agent such as a dihalide or an epoxyhalide, e.g. ethylene dichloride or epichlorohydrin and thereafter, with phosphorous acid and formaldehyde. Thus, for example, triethylenetetramine is reacted with epichlorohydrin in an approximately one to one mole ratio; thereafter the product is reacted with phosphorous acid, and formaldehyde in the presence of hydrochloric acid. The resulting methylenephosphonated polyamine is useful in small amounts as a scale inhibitor, being employed at concentrations of 20-50 ppm.

It has now been found that a particular heterocyclic nitrogen-containing compound, when polymerized by reacting it with ethylene dichloride, and subsequently phosphonomethylating with formaldehyde and phosphorous acid, will provide a threshold inhibiting product of superior ability.

SUMMARY OF THE INVENTION

Polymethylenephosphonic acid derivatives of polymers of aminoethylpiperazine have been found to be superior scale inhibitors. The polymers are formed by reacting aminoethylpiperazine with a dihalo, diepoxy or epoxyhalo compound and then reacting the resulting polymer with phosphorous acid and formaldehyde to form the polymethylenephosphonic acid polyamine of the invention.

DETAILED DESCRIPTION OF THE INVENTION

The polymers of the present invention are made by reacting aminoethylpiperazine (AEP) with a dihalo, diepoxy or epoxyhalo compound and subsequently reacting the polymer formed thereby with phosphorous acid and formaldehyde at a low pH, usually provided by the presence of a mineral acid, e.g. hydrochloric.

The AEP can be reacted with any number of dihalo, epoxyhalo or diepoxy compounds in order to form a dimer or polymer. Any suitable epihalohydrin may be reacted, epichlorohydrin being preferred. Other epichlorohydrin-type compounds include: 1,2-epoxy-4-chlorobutane, 2,3-epoxy-4-chlorobutane, 1,2-epoxy-5-chloropentane, 2,3-epoxy-5-chloropentane, etc. In general, the chloro derivatives are preferred, although the corresponding bromo or iodo compounds may be employed. Mixtures of epihalohydrins may also be employed.

Saturated dihalides having the formula $X(CH_2)_nX$, where X may be chlorine, bromine, iodine or combinations thereof and wherein n is an integer of from 1 to about 10, but preferably 2 to 6, may be employed. Thus, for example, methylene chloride, ethylene dichloride, 1,2- or 1,3-dichloropropane, 1,4- or 1,2-dibromobutane and the like may be employed.

Aralkylene dihalides can also be employed having the formula $X-H_2C-Ar-CH_2-X$ wherein Ar is

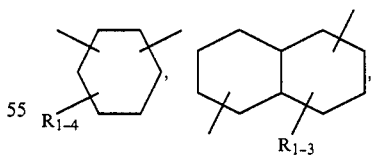

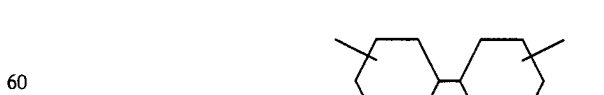

wherein R may be hydrogen, halogen, alkyl, having 1 to 4 carbon atoms, hydroxy and hydroxyalkyl, having 1 to 4 carbon atoms and X is a halogen atom.

Dihaloalkylene ethers can also be employed, e.g. bis(chloromethyl)ether or bis(chloroethyl)ether. Formulas for such ethers also include X—CH$_2$CH$_2$(OCH$_2$CH$_2$)$_n$X wherein n is 1 to 3 and

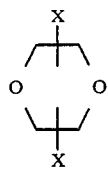

wherein X is a halogen atom.

The dihalides may also be unsaturated. Thus, 1,2-dichloroethylene, 1,4-dichloro-2-butene and the like may be employed.

The conditions for making the polymer are to employ the reactants in an amount of from about 0.2 to about 1 mole of the chain extender compound, preferably about 0.25 to about 0.6, i.e. the diepoxy-, dihalo- or epoxyhalo-compound, per mole of AEP. The temperature of reaction is from about 50° to about 100° C., preferably 70°–80° C. at a pressure sufficient to maintain the reactants in the liquid phase.

The phosphonomethylation (Mannich reaction) is then carried out on the product in the presence of a strong acid to maintain the pH at less than 1.

While the reaction will proceed at temperatures over a wide range, i.e., from 85° to 150° C., it is preferred that the temperatures of the reaction medium be maintained at the refluxing temperatures. The reaction is preferably conducted at atmospheric pressure, although subatmospheric and superatmospheric pressures may be utilized if desired. Reaction times will vary, depending upon a number of variables, but the preferred reaction time is 1 to 5 hours, and the most preferred reaction time is 2 to 4 hours.

Although the phosphorous acid or the formaldehyde may be added together or separately in any order to the reaction mixture, it is preferred to add the phosphorous acid to the polyamine and then to slowly add the formaldehyde under refluxing conditions.

Approximately equimolar amounts of formaldehyde and phosphorous acid are employed for the phosphonomethylation of the amine. Excess of either the aldehyde or acid can be utilized although large excesses of either would be uneconomical. The preferred process will use an amount of aldehyde equivalent to the amine hydrogens available and a slight stoichiometric excess of the phosphorous acid.

Although formaldehyde is preferred, other aldehydes may be employed in place of formaldehyde such as acetaldehyde, propionaldehyde and the like wherein the aldehyde may contain a straight or branched chain containing up to about ten carbon atoms.

Thus, the compounds of the present invention can be represented by the formula

wherein A is an organic radical having the formula

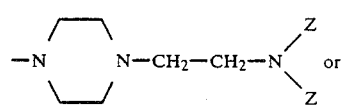

-continued

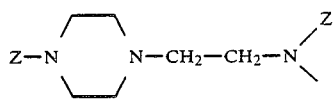

wherein Z is hydrogen, hydroxyethyl, hydroxypropyl,

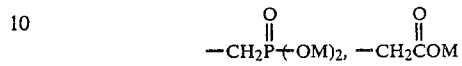

or BA wherein M is hydrogen, an alkali metal or ammonium, and wherein B is a divalent radical derived from a dihalo, diepoxy or haloepoxy organic compound having one of the following structures

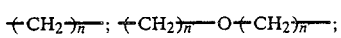

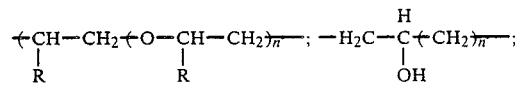

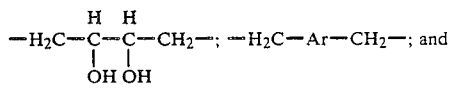

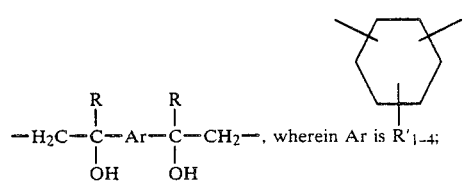

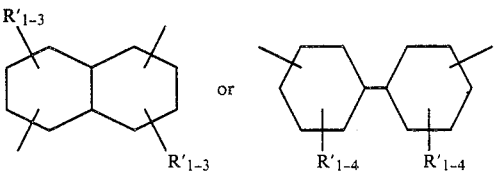

wherein n is 1–10, n' is 1–3, and wherein R is hydrogen or methyl and R' is hydrogen, an alkyl radical or a hydroxyalkyl radical having 1 to 4 carbons, a hydroxy radical or a halogen atom, m is 1–10 and at least 50% of the Z groups are

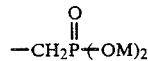

groups.

Preferred compounds of the invention are those wherein the B moiety is derived from epichlorohydrin or ethylene dichloride, wherein m is 1 or 2, the Z moiety is

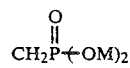

and M is H, Na or NH$_4$.

The following examples illustrate the invention:

EXAMPLE 1

An aminoethylpiperazine (AEP) based amine was prepared by reacting 22.7 g of aminoethylpiperazine (0.176 mole), 9.8 g of ethylene dichloride (EDC) (0.099 mole), and 17.5 g of deionized water (EDC/AEP mole ratio=0.56) in a 500-ml round-bottom reaction flask equipped with a water-cooled reflux condenser, mechanical stirrer, thermometer with a temperature controller, and an addition funnel. The reaction product was then phosphonomethylated by adding approximately 75 g of concentrated hydrochloric acid and 32.6 g (0.40 mole) of phosphorous acid to the aqueous amine solution and the reaction mixture heated to reflux and maintained for one hour. Aqueous 37% formaldehyde solution (28.1 g–0.35 mole) was added through the addition funnel over a one and one-half hour period. The reaction mixture was heated at reflux for an additional three hours and then cooled. The product was evaluated in the scale inhibition test (see Test Procedure following) and compared with diethylenetriaminepentamethylenephosphonic acid (DETA-MPA), a commercially available organophosphonic acid. The results are tabulated in Table I.

EXAMPLE A (COMPARATIVE)

Deionized water (100 g) and 32.7 g (0.25 mole) of 98% aminoethylpiperazine were weighed into a 500-ml round-bottom reaction flask equipped with a water-cooled reflux condenser, mechanical stirrer, thermometer with a temperature controller, and an addition funnel. Approximately 90 g of concentrated hydrochloric acid and 73.5 g (0.90 mole) of phosphorous acid were added to the aqueous amine solution. Heating and refluxing were carried out as in Example 1 and then 63.3 g (0.78 mole) of 37% aqueous formaldehyde was added through an addition funnel over one and one-half hours. The reaction mixture was heated at reflux as in Example 1 and cooled. Scale inhibition results, using the following test procedure, are shown in Table I.

| TEST PROCEDURE (Scale Inhibition) | | | |
|---|---|---|---|
| Solution A: | 0.02M CaCl$_2$.2H$_2$O 0.48M NaCl | Solution B: | 0.04M NaHCO$_3$ 0.48M NaCl |
| Titrant: | 0.01M EDTA | Indicator: | Murexide* |

*The indicator is a 0.2% solution of ammonium purpurate in ethylene glycol.

Inhibitor solutions were prepared from the compounds to be evaluated so that a solution with 1% active (as the acid) product was formed.

PROCEDURE

To a 4-ounce (118 ml) wide-mouth bottle was added 50 ml of solution A and a 1" teflon-coated magnetic stirring bar. To solution A, while stirring, was added 0.1 ml of the 1% solution of the compound to be tested. Stirring was continued for approximately one minute, then 50 ml of solution B was added and stirring continued for another three minutes. The stirring bar was removed, the bottle capped, labelled, and placed in an 80° C. oven for 24 hours. At the end of 24 hours the sample was removed from the oven and 5 ml of the liquid was extracted (avoiding particulates) and filtered through a 4-micron glass frit. To the filtered sample was added 2 ml 1N NaOH and 4 drops of 0.2% Murexide indicator solution. About 70 ml of deionized water was added and the solution titrated with 0.01M EDTA until the color changed from pink to violet.

The total calcium concentration is 0.01M after mixing 50 ml of solution A with 50 ml of solution B. If all of the calcium remains in solution during the 24-hour period at 80° C., then the concentration will still be 0.01M and this represents 100% inhibition of CaCO$_3$. Depending on the performance of the inhibitor being evaluated, some CaCO$_3$ will precipitate, leaving less soluble calcium. The titration measures the amount of soluble calcium left in solution after 24 hours at 80° C. This amount is divided by the total amount originally added and the result multiplied by 100 to obtain the percent inhibition.

The concentration of inhibitor employed in the scale inhibition test was 10 ppm (active acid) based on total weight of solution.

TABLE I

| Example | % Inhibition |
|---|---|
| 1 | 84 |
| A (Comp.) | 46 |
| DETA—MPA (Comp.) | 70 |

In the following examples different mole ratios of EDC/AEP were used. The procedure of Example 1 was followed except for the reactant ratios. Again, 10 ppm of the inhibitor was used. Results are given in Table II.

TABLE II

| Example | EDC/AEP mole ratio | Percent Inhibition |
|---|---|---|
| 2 | 0.26 | 89 |
| 3 | 0.46 | 89 |
| 1 | 0.56 | 84 |
| 4 | 0.81 | 75 |
| 5 (comparative) | 1.26 | 50 |
| Blank | (No additive) | 37 |

It is apparent from the data in the above tables that AEP trimethylenephosphonic acid (Example A) possesses only slight ability to inhibit scale, 46% as compared to no inhibitor at 37%. It can also be seen that the products formed by employing mole ratios of EDC/AEP of from about 0.2 to about 0.8 after phosphonomethylation give an unexpected result when compared to the phosphonomethylated DETA and AEP. It should also be noted that when higher polymers are formed, as in Table II, Example 5, inhibition is about that of the AEP monomer and is only slightly better than no additive at all.

EXAMPLE 6

Epichlorohydrin was substituted for the ethylene dichloride of Example 1 at a mole ratio of epi/amine of 0.50. The resulting methylene phosphonated product at 10 ppm provided 96% inhibition in the scale inhibition test.

The phosphonomethylated products of the invention are employed in amounts less than stoichiometric, i.e., "threshold amounts". The exact amount will depend on the concentration of metal ions which it is desired to control, but amounts as low as 0.1 ppm or as high as 500 ppm may be employed, based on the weight of solution.

We claim:

1. The phosphonomethylated product of the reaction of (1) aminoethylpiperazine with (2) a dihalo saturated or unsaturated aliphatic hydrocarbon having from 2 to 6 carbon atoms or a haloepoxy saturated aliphatic hydrocarbon having from 3 to 5 carbon atoms wherein the mole ratio of dihalo or haloepoxy compound to the amine compound is from about 0.20 to about 0.80.

2. The compounds represented by the formula

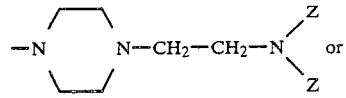

wherein A is an organic radical having the formula

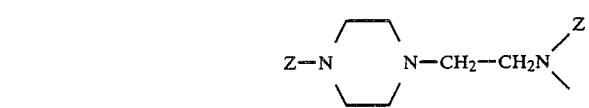

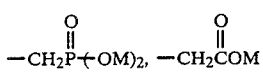

wherein Z is hydrogen, hydroxyethyl, hydroxypropyl, $$-CH_2\overset{O}{\overset{\|}{P}}(OM)_2, \quad -CH_2\overset{O}{\overset{\|}{C}}OM$$

or BA wherein M is hydrogen, an alkali metal or ammonium, and wherein B is a divalent radical derived from a dihalo or haloepoxy organic compound having the structure

wherein n is 2–10, n' is 1–3, and m is 1–10 and at least 50% of the Z groups are $$-CH_2\overset{O}{\overset{\|}{P}}(OM)_2$$

groups

3. The compound of claim 2 wherein m is 1 or 2, B is

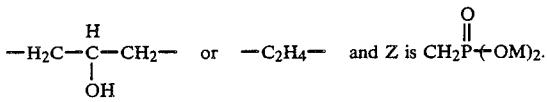

* * * * *

UNITED STATES PATENT AND TRADEMARK OFFICE
CERTIFICATE OF CORRECTION

PATENT NO. : 4,489,203
DATED : December 18, 1984
INVENTOR(S) : David A. Wilson and Druce K. Crump It is certified that error appears in the above—identified patent and that said Letters Patent is hereby corrected as shown below:

On page one, in the first line of the title, change "POLYUMERIC" to --POLYMERIC--.

Col. 1, first line of the title, change "POLYUMERIC" to --POLYMERIC--.

Signed and Sealed this

Third Day of September 1985

[SEAL]

Attest:

DONALD J. QUIGG

Attesting Officer    Acting Commissioner of Patents and Trademarks - Designate

UNITED STATES PATENT AND TRADEMARK OFFICE
CERTIFICATE OF CORRECTION

PATENT NO. : 4,489,203
DATED : December 18, 1984
INVENTOR(S) : David A. Wilson and Druce K. Crump It is certified that error appears in the above-identified patent and that said Letters Patent is hereby corrected as shown below:

On page one, in the first line of the title, change "ALKYLENE PHOSPHORIC" to --ALKYLENEPHOSPHONIC--.

Col. 1, first line of the title, change "ALKYLENE PHOSPHORIC" to --ALKYLENEPHOSPHONIC--.

Signed and Sealed this

Twenty-second Day of October 1985

[SEAL]

Attest:

Attesting Officer

DONALD J. QUIGG

Commissioner of Patents and
Trademarks—Designate